(12) United States Patent
Kurzweil et al.

(10) Patent No.: US 10,182,944 B2
(45) Date of Patent: Jan. 22, 2019

(54) SLEEP AIDE DEVICE

(71) Applicants: Raymond C. Kurzweil, Newton, MA (US); Sonya Kurzweil, Newton, MA (US)

(72) Inventors: Raymond C. Kurzweil, Newton, MA (US); Sonya Kurzweil, Newton, MA (US)

(73) Assignee: Kurzweil Technologies, Inc., Wellesley Hills, MA (US)

( * ) Notice: Subject to any disclaimer, the term of this patent is extended or adjusted under 35 U.S.C. 154(b) by 173 days.

(21) Appl. No.: 14/053,731

(22) Filed: Oct. 15, 2013

(65) Prior Publication Data

US 2014/0126738 A1    May 8, 2014

Related U.S. Application Data

(63) Continuation of application No. 10/179,486, filed on Jun. 24, 2002, now Pat. No. 8,559,649.

(51) Int. Cl.
| | |
|---|---|
| *G10K 11/16* | (2006.01) |
| *A61F 11/14* | (2006.01) |
| *A61F 11/12* | (2006.01) |
| *H04R 1/10* | (2006.01) |
| *G10K 11/178* | (2006.01) |

(52) U.S. Cl.
CPC .............. *A61F 11/14* (2013.01); *A61F 11/12* (2013.01); *G10K 11/178* (2013.01); *H04R 1/10* (2013.01);
(Continued)

(58) Field of Classification Search
CPC ............ G10K 11/178; G10K 11/1788; G10K 2210/116; G10K 11/175; G10K 2210/10; G10K 2210/1081; G10K 2210/12; G10K 2210/3028; G10K 2210/3045; G10K 2210/3216; G10K 2210/3219;
(Continued)

(56) References Cited

U.S. PATENT DOCUMENTS

| | | |
|---|---|---|
| 2,696,007 A | 12/1954 | Larkin et al. |
| 3,306,991 A | 2/1967 | Wood |
| 4,156,118 A | 5/1979 | Hargrave |

(Continued)

*Primary Examiner* — Lun-See Lao
(74) *Attorney, Agent, or Firm* — Fish & Richardson P.C.

(57) ABSTRACT

In one aspect, the invention is a sleep device. The sleep-aide device includes a soft housing adapted to be disposed over a user's head, a microphone positioned on the housing to receive an ambient sound signal, a suppression circuit that receives the ambient sound signal and produces a suppression sound signal, and a set of transducers, arranged in the soft housing, which receive the suppression sound signal. The suppression sound signal has a magnitude and phase to substantially cancel the ambient sound signal at the user's ear.

In another aspect, the sleep-aide device includes a microphone to receive an ambient sound signal, a suppression circuitry, which receives the ambient sound signal and transmits a suppression sound signal based on the ambient sound signal, and a transducer which receives the suppression sound signal, which has a magnitude and phase to substantially cancel the ambient sound signal at the user's ear. The sleep device also includes an earphone housing, which is attached to the ear when worn by a user, containing the microphone, the suppression circuitry and the transducer.

28 Claims, 4 Drawing Sheets

(52) U.S. Cl.
CPC ...... *H04R 1/1083* (2013.01); *A61F 2011/145* (2013.01); *G10K 2210/116* (2013.01); *H04R 1/1008* (2013.01)

(58) Field of Classification Search
CPC .............. G10K 2210/3221; H04R 1/46; H04R 2205/041; H04R 2225/41; H04R 2410/01; H04R 2420/03; H04R 2460/03; H04R 25/04; H04R 25/505; H04R 25/554; H04R 1/1008; H04R 1/1041
USPC ....... 381/71.1–71.6, 71.11–71.14, 94.1–94.1, 381/94, 72, 74, 92, 91, 370–373; 181/182; 128/848, 846
See application file for complete search history.

(56) References Cited

U.S. PATENT DOCUMENTS

| | | | |
|---|---|---|---|
| 5,133,017 A * | 7/1992 | Cain | G01R 33/3854 381/71.4 |
| 5,305,387 A | 4/1994 | Sapiejewski | |
| 5,477,867 A | 12/1995 | Balkanyi | |
| 5,787,894 A | 8/1998 | Holt | |
| 5,844,996 A * | 12/1998 | Enzmann | A61B 5/7475 381/71.11 |
| 5,881,390 A * | 3/1999 | Young | A41D 20/00 2/209.13 |
| 6,035,047 A * | 3/2000 | Lewis | G04G 13/021 340/4.1 |
| 6,088,836 A | 7/2000 | de Cordova | |
| 6,597,792 B1 | 7/2003 | Sapiejewski et al. | |
| 6,683,965 B1 * | 1/2004 | Sapiejewski | H04R 1/1083 381/370 |
| 6,748,087 B1 * | 6/2004 | Jones | G10K 11/1788 381/371 |
| 6,801,629 B2 * | 10/2004 | Brimhall | A61F 11/08 381/72 |
| 7,103,188 B1 * | 9/2006 | Jones | G10K 11/178 381/71.13 |
| 2002/0157168 A1 | 10/2002 | Andrews | |

* cited by examiner

SLEEP AIDE DEVICE

BACKGROUND

This invention relates to a sleep-aide device.

Getting a good night's sleep is important for a person's health. Studies have shown that people function better with uninterrupted sleep. Many things can cause a sleepless night. For example, an old mattress, caffeine, sleep apnea or poor health can contribute to sleeplessness. Another cause of sleeplessness is noise, such as snoring from a partner, aircraft, or automobile traffic. Other studies have shown that sleeping on one's side is an optimum sleep position.

Noise cancellation devices have existed for many years. Noise canceling headphones include microphones, which receive external sounds; circuitry, which predicts a future signal and generates a signal opposite of the predicted future sound signal; and speakers, which generate the opposite predicted signal. The construction of these devices include hard plastic housings for the speakers, microphones and circuitry. Since the hard plastic housings include speakers, the housing is designed to be placed over the user's ear. Some of these devices include ports for receiving audio signals.

SUMMARY

In one aspect, the invention is a sleep device. The sleep-aide device includes a soft housing adapted to be disposed over a user's head, a microphone positioned on the housing to receive an ambient sound signal, a suppression circuit that receives the ambient sound signal and produces a suppression sound signal, and a set of transducers, arranged in the soft housing, which receive the suppression sound signal. The suppression sound signal has a magnitude and phase to substantially cancel the ambient sound signal at the user's ear.

In another aspect, the sleep-aide device includes a microphone to receive an ambient sound signal, a suppression circuitry, which receives the ambient sound signal and transmits a suppression sound signal based on the ambient sound signal, and a transducer which receives the suppression sound signal, which has a magnitude and phase to substantially cancel the ambient sound signal at the user's ear. The sleep device also includes an earphone housing, which is attached to the ear when worn by a user, containing the microphone, the suppression circuitry and the transducer.

In still another aspect, the invention is a method of aiding sleep. The method includes receiving an ambient signal from a microphone located in a soft housing, and transmitting a suppression signal to a transducer by using a suppression circuitry. The suppression signal is based on the ambient signal received from the microphone and has a magnitude and phase to substantially cancel the ambient sound signal at the user's ear.

The aspects above may have some or all of the following advantages. The sleep-aide device allows a user to sleep without ambient sounds such as snoring or traffic disturbing the wearer. The sleep-aide device allows the wearer to sleep on their ears without discomfort from a hard casing pushing into the ears. Thus, a wearer is not restricted to sleeping on their back as hard-cased noise cancellation devices force the wearer to do. In addition, there are no exterior wires on the sleep-aide device that are a choking hazard. The sleep-aide aide device also allows the user to listen to selected forms of sounds such as music or a radio broadcast clearly without exterior ambient sounds interfering.

DESCRIPTION

Figure 1:
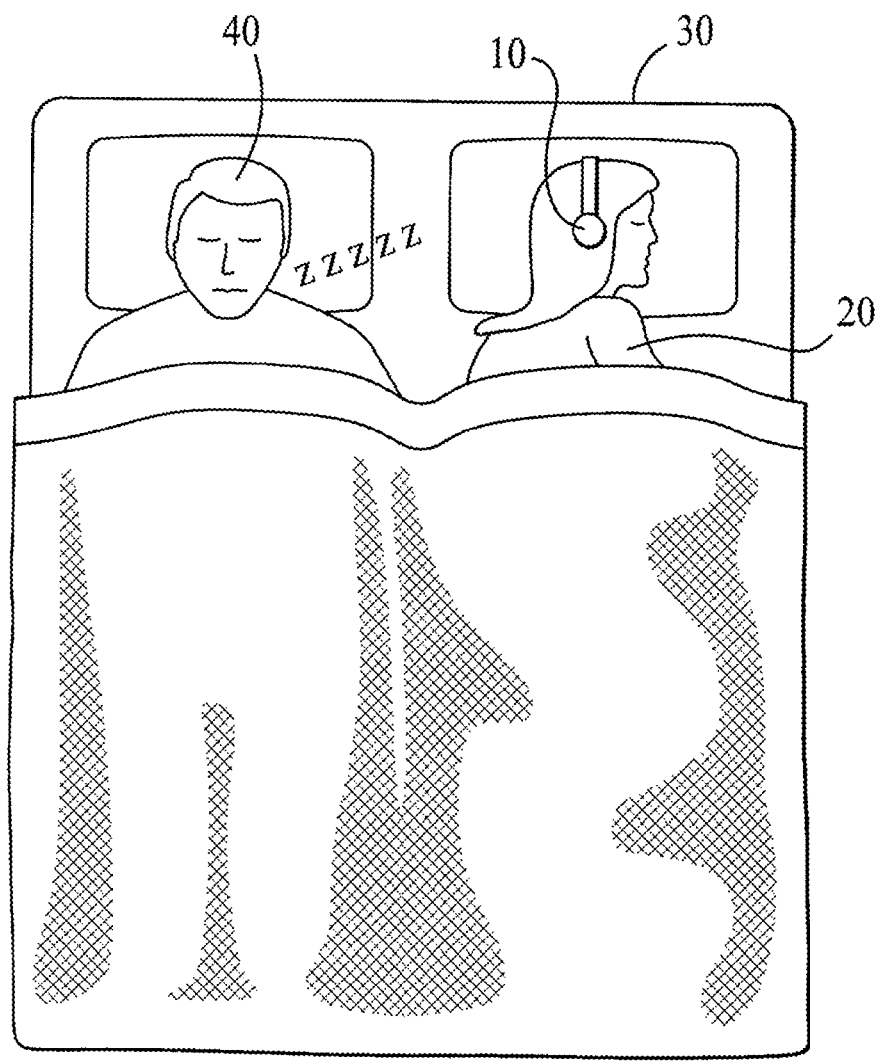
FIG. 1 is a sleep-aide device in a bedroom environment.
Figure 2A:
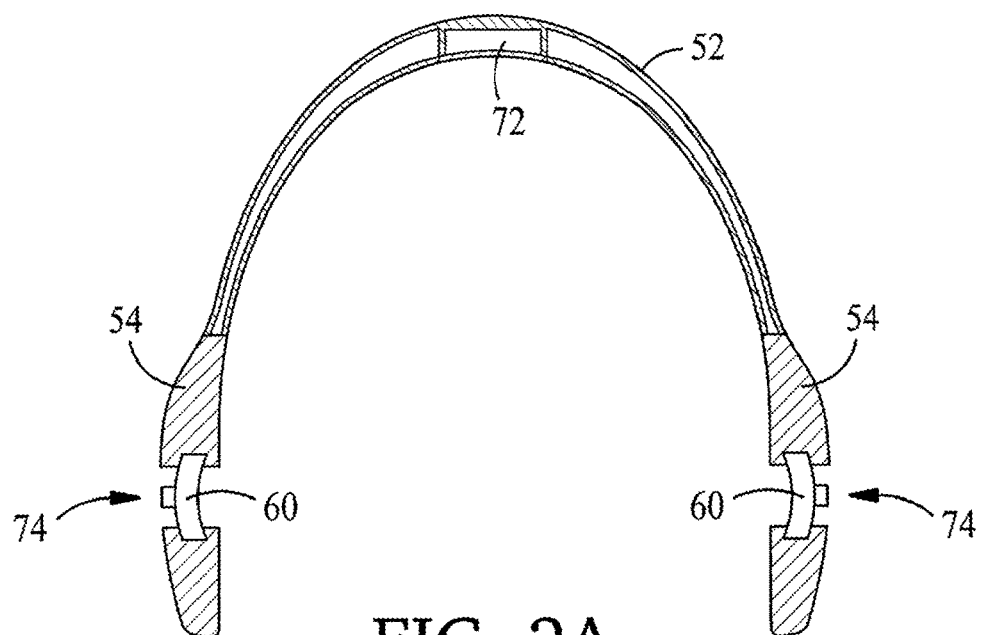
FIG. 2A is a cross-sectional view of the sleep-aide device.
Figure 2B:
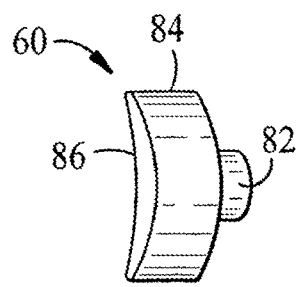
FIG. 2B is a cross-sectional view of circuitry of the sleep-aide device.
Figure 2C:
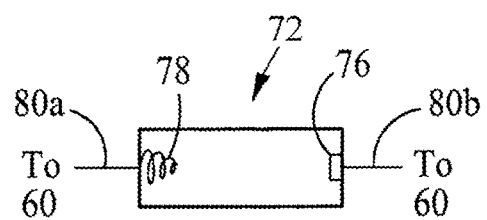
FIG. 2C is a top view of a battery compartment.

Referring to FIGS. 1, 2A, 2B and 2C, a sleep-aide device 10 is worn on a head of a user 20 while sleeping in a bed 30. Sleep-aide device 10 neutralizes ambient sounds such as snoring from a partner 40 so that the user may sleep without disturbance from these ambient sounds. Device 10 includes a housing 52; padding 54; a pair of electrical components 60, one for each ear of the user; and a battery compartment 72, which is positioned on the top of housing 52. Housing 52 is shaped similar to regular headphones. Each set of electrical components 60 include transducers 86 that deliver cancellation sound to a user's ear. Electrical components 60 are nestled within padding 54 so that when housing 52 is placed over the user's head, electrical components 60 rest comfortably over the user's ear even when the user is sleeping on the ear. Housing 52 is comprised of elastic materials to allow the user to place transducers 86 over the user's ears and hold the speakers securely over the ears. Padding 54 is made from soft and elastic materials so that the padding cushions electrical components 60 against the user's ear and prevents the hard casing from the electrical components from causing discomfort on the ears of the user. Thus, the user can sleep on their side or on their stomach while using sleep-aid device 10 whereas noise cancellation devices without the proper cushioning forces the user to sleep on their backs.

Each set of electrical components 60 also includes a microphone 82 and a suppression circuit 84. Wiring (not shown) within housing 52 interconnects microphone 82 to suppression circuit 84, suppression circuit 84 to transducer 86, and batteries (not shown) to electrical components 60. The batteries are housed in battery compartment 72. Battery compartment 72 has a positive terminal 76 and a negative terminal 78. Positive terminal 76 and negative terminal 78 are electrically connected to electrical components 60 by wires 80a and 80b. Thus, all the wiring to sleep-aide device 10 is internal to housing 52. During a typical night's sleep, a person changes positions every few hours. By eliminating external wires, possible discomfort or disturbance of sleep is eliminated from entanglement within the wires. Further, there is no opportunity for the user to have an external wire wrap around the user's neck and cause choking of the user.

Figure 3B:
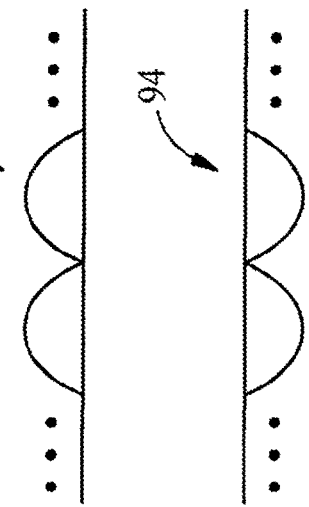
FIG. 3B depicts the way form before a suppression circuit and a waveform after the suppression circuit.
Figure 3A:
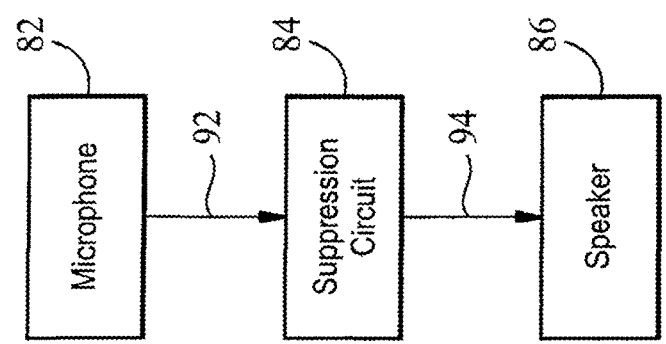
FIG. 3A is flow chart depicting the functionality of the sleep-aide device circuitry.

Referring to FIGS. 3A and 3B, microphone 82 receives an ambient sound signal 92. Microphone 82 is positioned such that the microphone can receive ambient sounds that are present in the user's environment. Microphone 82 receives ambient sound signal 92 through an opening 74 in padding 54. Ambient sound signal 92 can be a sound of a partner snoring or the sound of traffic. Suppression circuit 84 generates an inverse signal 94 of ambient signal 92. Inverse signal has substantially the opposite phase and the same magnitude as the ambient sound that reaches the user's ears to substantially cancel ambient sound signal 92 at the user's ears. Suppression circuit 84 includes an amplifier (not shown), to amplify the ambient sound signal. The inverse signal 94 is transmitted to transducer 86 for transmission to the user's ear. In other embodiments, the amplifier is separate from suppression circuit 84 and boosts inverse signal 94 to speakers 86. In other embodiments, the batteries are co-located inside suppression circuit 84.

In other embodiments, sleep-aide device 10 includes a jack (not shown) connected to speaker 86. The jack allows sleep-aide device to be connected to a compact disc (CD) player, a radio or any other external device. In conjunction with the noise cancellation feature of sleep-aide device 10, the user can hear music, for example, without the interference from airplanes or snoring. In addition, the user can listen to the music while sleeping on their side or on their stomach.

In still further embodiments, a receiver (not shown) is located within electrical components 60 and connected to transducer 86. The receiver receives wireless signals from an external device (not shown), such as CD player or a radio. Thus, the user has no external wires that pose as a choking hazard during sleep while listening to music. In other embodiments, housing 52 is a sleeping bonnet.

Figure 4:
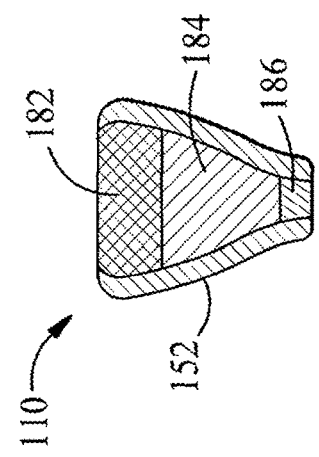
FIG. 4 is another embodiment of a sleep-aide device.

Referring to FIG. 4, in other embodiments, a sleep-aide device 110 includes a microphone 182, a suppression circuit 184 and a speaker 186 each of which are housed within a soft housing 152. Soft housing 152 fits securely within an ear canal much like a hearing aid. Housing 152 is made of soft elastic material to allow the user to sleep on the ear when sleep-device 110 is placed within the ear canal without discomfort to the user. Suppression circuit 184 includes a battery cell (not shown) for providing sufficient power to drive the suppression circuit and send signals to speaker 186. In other embodiments, sleep-aide device 110 includes a receiver (not shown) that receives wireless transmissions from an exterior device (not shown) such as a CD player or a radio. In still other embodiments, housing 152 can allow sleep-aide device 110 to be attached over the ear.

Figure 5A:
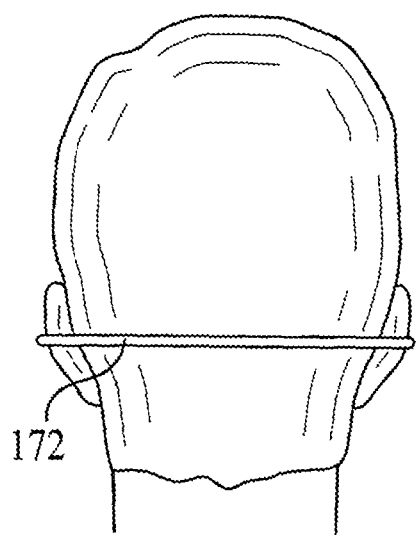
FIGS. 5A-5B are another embodiment of a sleep-aide device.
Figure 5B:
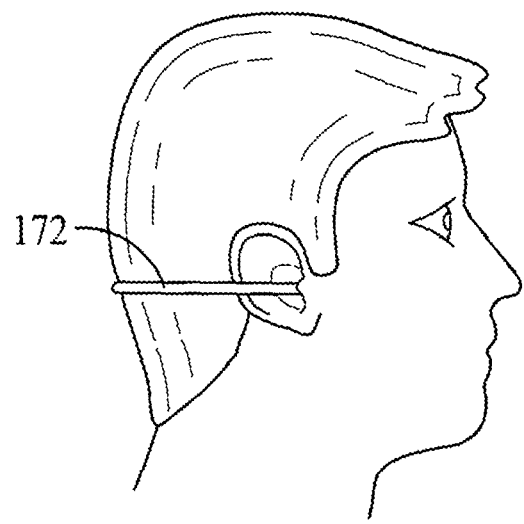

Referring to FIGS. 5A and 5B, sleep-aid device 110 are typically used alone, but may be used in pairs. For example, a string 172, with each end attached to a sleep device 110 can be used to keep two sleep-aide devices 110 from separating from the other device. String 172 has each end attached to a different sleep-aide device 110 and in use is worn in the back of the wearer's head. Other embodiments not described herein are also within the scope of the following claims.

What is claimed is:

1. A sleep-aide device, comprising:
a housing containing soft and elastic padding material, the housing adapted to be placed on and about a user's head;
a pair electrical component circuit sets supported within the soft and elastic padding material on each a pair of opposing ends of the housing, with each electrical component circuit set comprising:
a microphone configured to receive an ambient sound signal;
a sound suppression circuit carried by the housing and configured to receive the ambient sound signal from the microphone, and the circuit configured to produce a suppression sound signal having an electrical phase angle that is substantially opposite to that of the ambient sound signal; and
a transducer positioned in the soft and elastic padding material, and supporting the microphone and the suppression circuit, the transducer packaged in a corresponding hard casing, the transducer arranged in the housing in a position approximating a position of a user's ear when the sleep-aid device is placed on and about the user's head;
wherein the padding in the housing nestling and cushioning the transducer of each of the pair of electrical component circuit sets such that the padding inhibits the hard casing of each transducer from compressing against the user's ears when external pressure is applied to the housing against the user's head, the transducer of each of the pair of electrical component circuit sets configured to receive the suppression sound signals, and produce acoustic energy in response to the suppression sound signals having a magnitude and phase to substantially cancel the ambient sound signal at a user's ear; and
a battery compartment on an exterior portion of the housing, midway of the electrical component circuit sets.

2. The sleep-aide device of claim 1 wherein the soft padding material is placed within the soft housing in locations corresponding to locations where the pair of transducers would be urged against the ears of a user.

3. The sleep-aide device of claim 1, further comprising an amplifier for amplifying the suppression sound signals received from the suppression circuits.

4. The sleep-aide device of claim 1 wherein the ambient sound signal is a snoring signal.

5. The sleep-aide device of claim 1 wherein the ambient sound signal is a traffic noise signal.

6. The sleep-aide device of claim 1 wherein the suppressive sound signal is an inverted signal of a predicted sound signal.

7. The sleep-aide device of claim 6 wherein the predicted sound signal is calculated based on the ambient sound signal.

8. The sleep-aide device of claim 1 wherein the housing is a sleeping bonnet.

9. The sleep aide device of claim 1 wherein each of the pair of electrical component circuit sets are configured as earpieces, and the housing, comprises:
a band to couple the earpieces, with the band adaptable to be worn about the user's head, and with the band supporting the microphone.

10. The sleep-aide device of claim 1, where the
battery compartment has terminals coupled to wires that are disposed through the soft housing and connected to the suppression circuits of each of the pair of electrical component circuit sets.

11. The sleep-aide device of claim 1, further comprising:
a receiver receiving sounds signals from an exterior transmitter, the receiver relaying the information to the transducer.

12. A sleep-aide device, the device comprising:
a housing configured to be worn over a user's head, the housing comprising soft and elastic padding material;
a microphone to receive an ambient sound signal, the microphone positioned at a middle portion of the housing, and positioned on an exterior portion of the housing;
a suppression circuitry, receiving the ambient sound signal and transmitting a suppression sound signal based on the ambient sound signal; and a pair of transducers embedded in the housing, each transducer of the pair being equidistant from the microphone, with each transducer receiving the suppression sound signal, and producing acoustic energy in response to the suppression sound signal having a magnitude and phase to substantially cancel the ambient sound signal at the user's ear, the pair of transducers arranged in the housing in positions approximating positions of a user's ears when the sleep-aid device is worn over the user's head, and with each of the transducers being embedded within the soft and elastic padding material to inhibit the pair of transducers from compressing against the user's ears when external pressure is applied to the housing.

13. The sleep-aide device of claim 12, further comprising an amplifier for amplifying the first suppression sound signal received from the first suppression circuitry.

14. The sleep-aide device of claim 12 wherein the ambient sound signal is a snoring signal.

15. The sleep-aide device of claim 12 wherein the ambient sound signal is a traffic noise signal.

16. The sleep-aide device of claim 12 wherein the suppression sound signal is an inverted signal of a predicted sound signal.

17. The sleep-aide device of claim 16 wherein the predicted sound signal is calculated based on the ambient sound signal.

18. A method of aiding sleep comprising:
receiving an ambient signal from a microphone located on an exterior portion of a soft housing, the housing comprised of soft and elastic padding material, the housing adapted to be placed on and about a user's head, with the housing supporting a pair of transducers positioned distally from the microphone, the pair of transducers nestled in the soft and elastic padding material of the housing such that the soft and elastic padding material inhibits the set of transducers from compressing against the user's ear when external pressure is applied to the housing, with the microphone being positioned on the exterior of the housing equally distant between the pair of transducers when the sleep-aid device is placed on and about the user's head; and
transmitting a suppression signal to the pair of transducers by using suppression circuitry, the suppression signal based on the ambient signal received from the microphone and producing acoustic energy having a magnitude and phase to substantially cancel the ambient sound at a user's ears.

19. The method of claim 18 wherein the soft and elastic padding material of the soft housing includes the soft and elastic padding material cushioning at locations where the housing would contact the ears of a user.

20. The method of claim 18, further comprising:
amplifying the first suppression signal received from the first suppression circuitry.

21. The method of claim 18 wherein receiving the ambient sound signal comprises receiving a signal corresponding to snoring.

22. The method of claim 18 wherein receiving the ambient sound signal comprises receiving a signal corresponding to traffic noise.

23. The method of claim 18 wherein transmitting the suppression signal comprises transmitting an inverted signal of a predicted sound signal.

24. The method of claim 23 wherein transmitting the inverted signal of a predicted sound signal comprises calculating the predicted sound signal based on the ambient sound signal.

25. The method of claim 18 wherein the soft housing is a sleeping bonnet that is placed over the user's head.

26. The method of claim 18, further comprising using a receiver to receive signals from an external device, the receiver electrically connected to the transducer.

27. The method of claim 18, further comprising using the soft housing to hold wires within the housing, the wires connecting the transducer, the suppression circuitry and the microphone.

28. The method of claim 18, further comprising using a transducer for receiving the suppression sound signal.

\* \* \* \* \*